United States Patent [19]

Christensen

[11] Patent Number: 4,622,961
[45] Date of Patent: Nov. 18, 1986

[54] ARM SLING WITH MITTEN POCKET

[76] Inventor: Margery Christensen, 121 Rosewood Dr., Bristol, Conn. 06010

[21] Appl. No.: 720,080
[22] Filed: Apr. 4, 1985
[51] Int. Cl.⁴ .............................................. A61F 5/40
[52] U.S. Cl. ...................................... 128/94; 128/77
[58] Field of Search ......... 128/94, 77, 87 R, DIG. 15; 2/270, 125, 111

[56] References Cited

U.S. PATENT DOCUMENTS

| | | | |
|---|---|---|---|
| 1,092,047 | 3/1914 | Hertz | 2/270 |
| 1,183,792 | 5/1916 | Arow | 2/270 |
| 2,274,510 | 2/1942 | Wohl | 2/270 |
| 2,306,715 | 12/1942 | Rubinstein | |
| 2,594,809 | 4/1952 | Sanders | |
| 3,815,588 | 6/1974 | Klausner | |
| 4,214,579 | 7/1980 | Ford | |
| 4,372,301 | 2/1983 | Hubbard et al. | |

Primary Examiner—Robert Peshock
Assistant Examiner—John G. Weiss

[57] ABSTRACT

An arm sling has an integral mitt section thereon which can be positioned to enable envelopment of either the forearm alone, or of the forearm and entire hand of the wearer. The mitt section can either extend from or be folded into the sleeve section of the cradle or body of the sling, thereby affording the two alternatives.

8 Claims, 6 Drawing Figures

ARM SLING WITH MITTEN POCKET

BACKGROUND OF THE INVENTION

Arm slings of the sort commonly used following injury or surgery must of course provide secure support and comfort to the wearer. Such slings are normally made of a fabric or other supple material, and for maximum comfort are generally provided with adjustable straps, and with padding at suitable locations.

Typically, arm slings have body portions that envelop and cradle the forearm of the wearer, leaving his hand free to protrude from the end. While this may be advantageous from the standpoint of permitting limited usage of the immobilized arm, it may also be quite undesirable, such as when the weather is cold. Frequently, the patient's hand will be at least partially covered by a plaster cast or bulky bandage, making use of a common glove or mitten difficult or impossible, and in any event rather inconvenient.

The need to protect the wearer's hand against the cold is recognized in Rubeninstein U.S. Pat. No. 2,306,715; he provides a glove, permanently or detachably secured to the body section of the sling described, for that purpose.

In Sanders U.S. Pat. No. 2,594,809 an arm sling is disclosed in which a piece of fabric is fixed to the forward edge portion of the bottom wall, for the purpose of simulating a shirt cuff and thereby concealing the identity of the sling.

Both Klausner U.S. Pat. No. 3,815,588 and Ford U.S. Pat. No. 4,214,579 disclose slings which have hand supporting portions with loops to receive the individual's fingers.

Hubbard et al disclose, in U.S. Pat. No. 4,372,301, an arm sling which utilizes a trough constructed of flexible material; the end portion can be folded inwardly to adapt the trough to forearms of different lengths.

Despite prior art activity such as the foregoing, a need remains for an effective and comfortable arm sling having means, conveniently disposed thereon, by which the hand of the patient can either be covered or exposed, as desired. For self-evident reasons, any such device must of course also be attractive and relatively inexpensive to produce.

Accordingly, it is a primary object of the present invention to provide a novel and highly comfortable arm sling having means thereon by which the patient's hand can either be exposed or covered, as desired.

It is also an object of the invention to provide such a sling which is convenient to use, of attractive appearance, and relatively facile and inexpensive to produce.

A more specific object of the invention is to provide an arm sling having the foregoing features and advantages, including a hand-receiving mitt section which can be neatly and conveniently folded out of the way when not in use.

SUMMARY OF THE INVENTION

It has now been found that the foregoing and related objects of the invention are readily attained by the provision of an arm sling comprised of a cradle member and an strap member, the cradle member having a sleeve section and a mitt section dimensioned and configured, respectively, to substantially receive the forearm and hand of the user. Each of the sections of the cradle member is comprised of a pair of substantially coextensive side panel portions. The panel portions of the mitt section are joined to one another about the exterior of the cradle member, and are disconnected internally thereof to permit insertion of the hand. The panel portions comprising the sleeve section are joined to one another along the bottom of the cradle member and are normally substantially disconnected along the top, and the panel portions of both sections, on at least one side of the cradle member, are connected to one another. Construction is such that the mitt section can be folded inwardly from an extended position to a position within the sleeve section, thereby adapting the cradle member to envelope either the forearm and hand of the user, or only his forearm, depending upon the disposition of the mitt section.

In the preferred embodiments, the panel portions of the two sections on one side of the cradle member will be disconnected from one another to permit their relative displacement, for inward folding of the mitt section in a desirable manner, and means will be provided for disengageably securing the cooperating panel portions together. The mitt section will advantageously be formed with a generally rectilinear edge substantially traversing the cradle member, about which inward folding of the mitt section will be effected. When (as will usually be the case) the cradle member is constructed from a supple fabric, the connected panel portions will desirably be joined by a transversely extending seam, which will serve both as a permanent attachment (as is preferred) and also to facilitate inward folding of the mitt section. The fabric employed will normally be of a heat insulating character, for warmth.

Opposite ends of the strap member will generally be connected adjacent the forward and rearward ends of the cradle member, which will for that purpose desirably have a strip of flexible material attached to the panel portions of its sleeve section and extending thereacross. The strap member will normally have means on at least one of its end portions for affixing elements thereof to one another in a multiplicity of relative positions, to thereby permit adjustment of its effective length. An elongated neck pad may be mounted upon the strap member, and slidable therealong to best accommodate variation of the effective strap length.

DETAILED DESCRIPTION OF THE ILLUSTRATED EMBODIMENT

Figure 1:
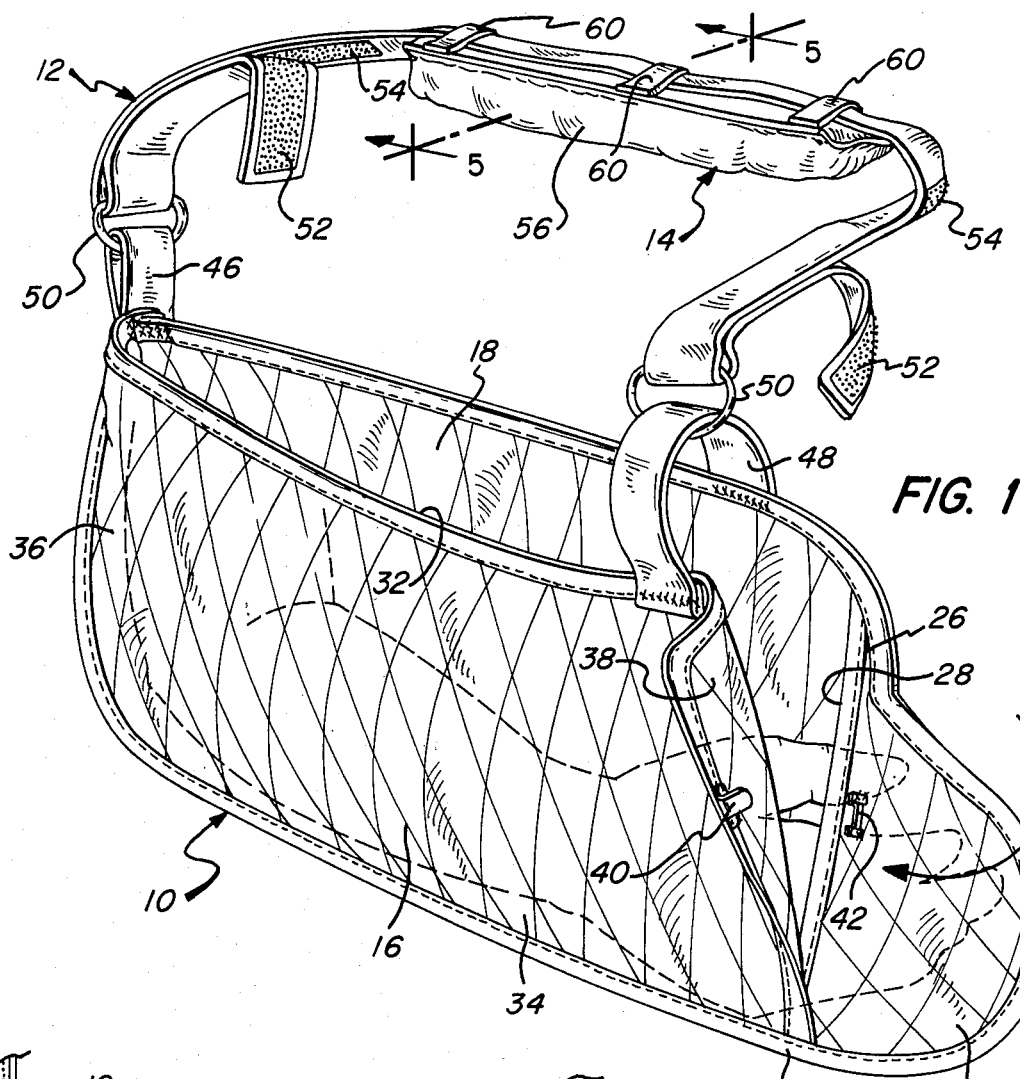
FIG. 1 is a perspective view of an arm sling embodying the present invention, with the outer panel portion and end elements of the strap member partially displaced from fully secured positions, and with the normal placement of the patient's arm shown in phantom line.
Figure 2:
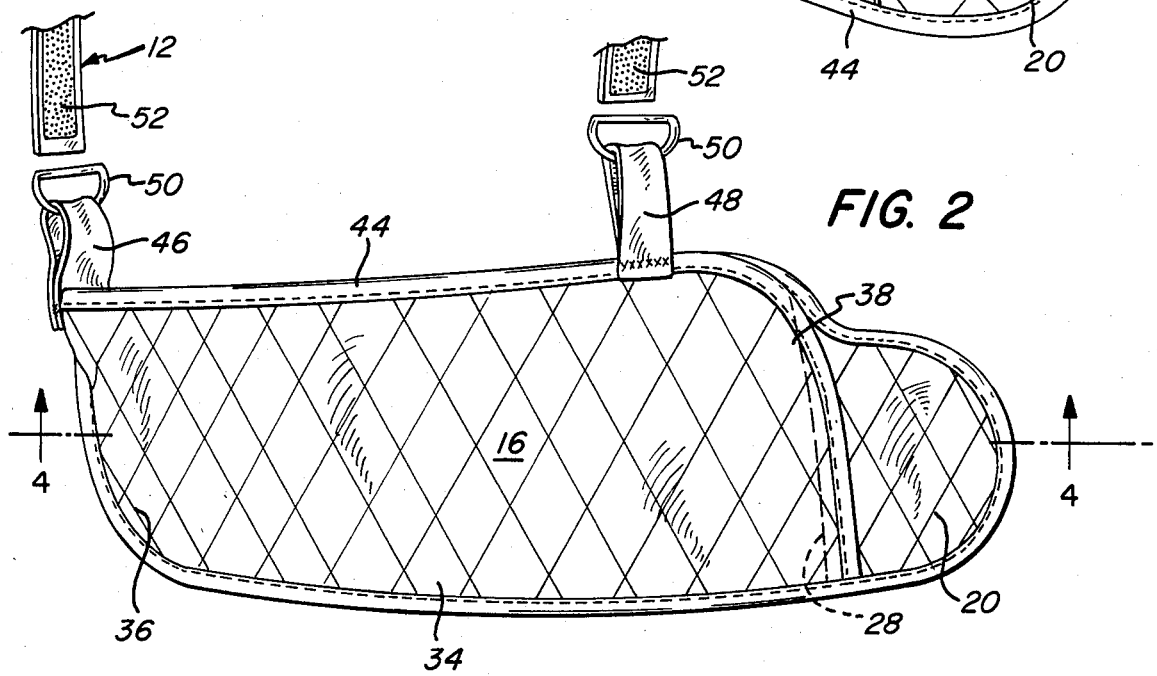
FIG. 2 is a fragmentary, outside elevational view of the sling of FIG. 1, drawn to a reduced scale.
Figure 3:
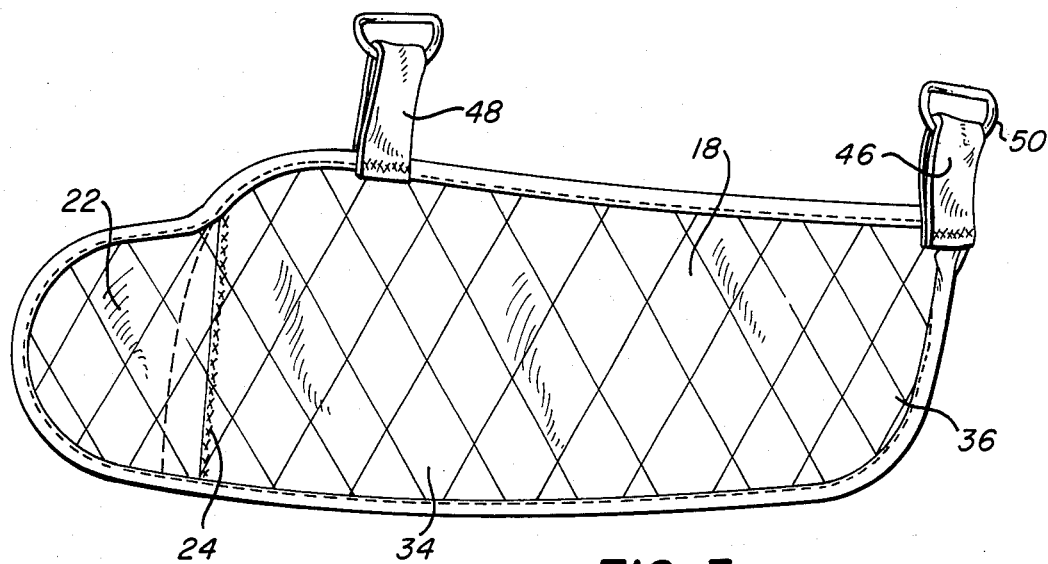
FIG. 3 is a corresponding inside elevational view of the cradle member of the sling.
Figure 4:
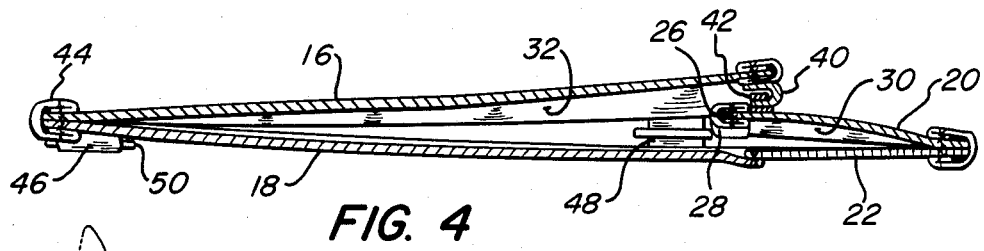
FIG. 4 is a sectional view of the cradle member taken along line 4—4 of FIG. 2.

Turning now in detail to the appended drawings, therein illustrated is an arm sling embodying the present invention, and consisting of a cradle member, a strap member, and a neck pad member, generally designated by the numerals 10, 12 and 14, respectively. The cradle member 10 is constructed of a warm and supple quilted fabric, and consists of generally coextensive sleeve section panel portions 16, 18, and mitt section panel portions 20, 22. In the form shown, the sling is specifically constructed to support the patient's right arm and hand, and therefore the portions 16, 20 will normally be on the outside and the portions 18, 22 on the inside of the sling. The inside panel portions 18, 22 are permanently connected to one another by a tranversely extending line of crease stitching at 24 (see FIG. 3). The two mitt section portions 20, 22 are peripherally secured to one another on the exterior of the member 10, with the free transverse marginal element 26 of the portion 20 providing a slit-like opening 28 into the hand-receiving mitt pocket 30, cooperatively defined therebetween.

A relatively large, envelope-like recess 32, defined between the sleeve section panel portions 16, 18 to receive the patient's forearm, is formed by joining the panel portions along their bottom and rear margins 34, 36, respectively. The upper edges of the sleeve section panel portions 16, 18 are disconnected from one another. A forward marginal element 38 of the outer panel portion 16 is also freely movable, cooperating elements 40, 42 of a hook and bar-type fastener being attached to the marginal elements 38, 26, respectively, so that they can be disengageably secured to one another in the overlapped relationship shown. The edges of the fabric panels are finished with lengths 44 of binding material, in conventional fashion.

A loop 46 of webbing is affixed to the rear upper margin of the cradle member 10, and a strip 48 thereof extends across the top of the member between the two panel portions 16, 18, the loop and strip 46, 48 each retaining a D-shaped ring 50 to receive one of the opposite ends of the neck strap member 12. End sections of the strap have cooperating panels 52, 54 of a hook-and-loop-type of fastening material (e.g., Velcro) secured on them to permit affixation in a range of positions, so as to thereby render the strap member 12 of readily variable effective length. The neck pad member 14 is also made of fabric panels 56, which are joined to form a cavity that is stuffed with wadding 58; three transverse strips 60 provide loops through which the strap member 23 passes, enabling the pad to be readily shifted to an optimal position, depending upon the adjusted length of the strap.

Figure 6:
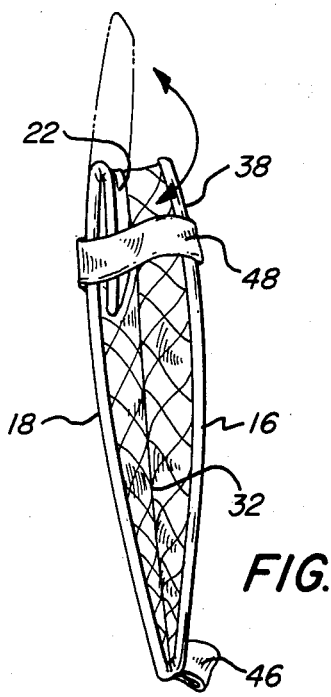
FIG. 6 is a plan view of the cradle member showing, in full and phantom line, respectively, the inwardly folded and extended positions of the mitt section.
Figure 5:
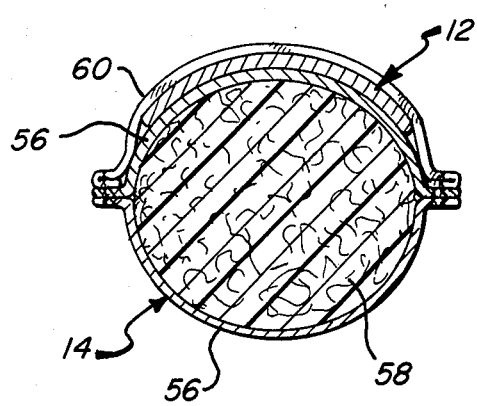
FIG. 5 is a sectional view of the strap and pad members employed in the sling, taken along line 5—5 of FIG. 1 and drawn to a greatly enlarged scale.

As seen in FIGS. 1-4, the mitt section of the cradle member 10, comprised of the panel portions 20, 22, is extended outwardly to position the pocket 30 to receive the patient's hand (essentially his fingers); the same position is shown in phantom line in FIG. 6. To expose his fingers, the user need only fold the mitt section inwardly (as facilitated by the line of crease stitching 24) to the position shown in full line in the latter Figure.

As indicated above, the embodiment of the sling illustrated is specifically designed for the arm on the right side of the patient; obviously, the cradle member may be constructed in mirror image form for left arm support. It will be appreciated that to render the sling most effective and comfortable it will generally be desirable to provide it in a range of sizes for both children and adults (e.g., small, medium and large), so as to best accommodate the patient's arm.

Although a preferred embodiment of the sling is described above and shown in the drawings, it will be understood that substantial variation is possible without departing from the underlying concepts of the invention. For example, web materials other than quilted fabrics can be used for the several panels of the cradle member and, indeed, combinations of different materials may be desirable for certain purposes. Also, rather than using several separate pieces to construct the cradle member, two or more of the panel portions may be provided as parts of a single web, suitably configured for that purpose. While it will generally be most convenient to join the panels by sewing them together, other means of attachment may be substituted, as appropriate. The design and trim features, the strap construction, and the hardware employed may of course vary widely.

Thus, it can be seen that the present invention provides a novel and highly comfortable arm sling having integral means thereon by which the patient's hand can either be exposed or covered, as desired. The sling is convenient to use, of attractive appearance, and relatively facile and inexpensive to produce. More specifically, it includes a hand-receiving mitt section which can be neatly and conveniently folded out of the way when not in use. Permanent attachment of the mitt will keep it readily available, without risk of loss or misplacement.

Having thus described the invention, what is claimed is:

1. An arm sling comprised of a cradle member and attached strap means, said cradle member having a sleeve section and, at the forward end thereof, an integral mitt section, said sleeve and mitt sections being dimensioned and configured, respectively, to substantially receive the forearm and hand of the wearer, each of said sections beign comprised of a pair of substantially coextensive side panel potions, said strap means being attached to both of said panel portions of said sleeve section adjacent said forward end thereof, as well as being attached adjacent the rearward end of said cradle member, said panel portions of said mitt section being joined to one another about the exterior of said cradle member, and being disconnected therewithin to permit insertion of the hand into said mitt section, said panel portions of said sleeve section being joined along the bottom and disconnected along the top, said panel portions of said sleeve and mitt sections, on one side of said cradle member, being joined to one another, and said panel portions of said sleeve and mitt sections on the other side being disconnected from one another to permit facile displacemnt of said sleeve panel portion one other side, relative to said sleeve panel portion on one side, with said strap means so attached, said sleeve panel portion on other side having disengageable means thereon for temporarily affixing them to one another, the construction of said cradle member permitting folding of said mitt section from an extended position to an inward position within said sleeve section by relative displacement of said sleeve and mitt panel portions on said other side, said cradle member thereby being adapted for facile conversion for enveloping the forearm and hand of the wearer, in said extended position of said mitt section, or alternatively, for enveloping substantially only the forearm in said inward position thereof.

2. The sling of claim 1 wherein said panel portion on said one side are permanently connected to one another.

3. The sling of claim 2 wherein said panel portion of said mitt section on said other side has a generally rectilinear edge substantially traversing said cradle member, the corresponding edge elements of said panel portions on said other side overlapping one another, and said cradle member construction facilitating inward folding of said mitt section about said rectilinear edge.

4. The sling of claim 1 wherein said cradle member is constructed substantially entirely from a supply fabric.

5. The sling of claim 4 wherein said panel portions on said one side are permanently connected by a seam extending transveresly of said cradle member to facilitate such inward folding of said mitt section.

6. The sling of claim 4 wherein said fabric is of a heat insulating character.

7. The sling of claim 1 wherein said strap means comprises an elongated strap member and a strip of flexible material attached to said panel portions of said sleeve section adjacent said forward end and extending across the top thereof, one end of said strap member being connected to said strip.

8. The sling of claim 1 wherein said strap member has at least one end portion with means thereon for affixing elements thereof to one another in a multiplicity of relative positions, to thereby permit adjustment of the effective length of said strap member, and wherein said sling additionally includes an elongated pad member slidably mounted upon said strap member to afford optimal positioning, depending upon the effective length to which said strap member is adjusted.

* * * * *

UNITED STATES PATENT AND TRADEMARK OFFICE
CERTIFICATE OF CORRECTION

PATENT NO. : 4,622,961
DATED : November 18, 1986
INVENTOR(S) : MARGERY CHRISTENSEN It is certified that error appears in the above—identified patent and that said Letters Patent is hereby corrected as shown below:

Column 4, line 39, "beign" should be -- being --;
          line 40, "potions" should be -- portions --;
          line 54, "displacemnt" should be -- displacement --;
          line 55, after portion "one" should be -- on --;

Column 5, line 1, "portion" should be -- portions --;
          line 11, "supply" should be -- supple --.

Signed and Sealed this

Thirty-first Day of March, 1987

Attest:

DONALD J. QUIGG

*Attesting Officer*      *Commissioner of Patents and Trademarks*